United States Patent

Hougham et al.

[11] Patent Number: 5,861,757
[45] Date of Patent: Jan. 19, 1999

[54] DYNAMIC SOLVENT PERMITTIVITY INSTRUMENT

[75] Inventors: Gareth Geoffrey Hougham, Ossining; Alfred Viehbeck, Fishkill; Stanley Joseph Whitehair, Peekskill, all of N.Y.

[73] Assignee: International Business Machine Corporation, Armonk, N.Y.

[21] Appl. No.: 758,123

[22] Filed: Nov. 25, 1996

[51] Int. Cl.$^6$ .................................................. G01N 31/06
[52] U.S. Cl. .......................... 324/672; 324/647; 324/679; 73/61.41
[58] Field of Search .............................. 73/64, 56, 61.41; 324/665, 666, 679, 680, 647, 672, 443

[56] References Cited

U.S. PATENT DOCUMENTS

| | | | |
|---|---|---|---|
| 2,800,628 | 7/1957 | Stinson | 324/665 |
| 3,215,931 | 11/1965 | Schooley | 324/665 |
| 3,437,446 | 4/1969 | Pierce | 324/443 |
| 4,047,100 | 9/1977 | Robinson | 324/443 |
| 5,239,862 | 8/1993 | Atkinson | 73/64.56 |

FOREIGN PATENT DOCUMENTS

| | | | |
|---|---|---|---|
| 1423952 | 9/1988 | U.S.S.R. | 324/665 |
| 675030 | 7/1952 | United Kingdom | 324/443 |

*Primary Examiner*—Josie Ballato
*Assistant Examiner*—Jose M. Solis
*Attorney, Agent, or Firm*—Daniel P. Morris

[57] ABSTRACT

An instrument for measuring the dielectric constant of samples with complex or uncertain geometries that can include unusually shaped single sample pieces or collections of differently shaped sample pieces such as powders. The premise of the measurement technique is that a reference capacitor plate and a sample capacitor plate are exposed to a dynamically-changing solvent mixture. When the capacitance of these two fixtures become equal at the point at which a particular solvent mixture is reached, the dielectric constant of the sample is then known.

22 Claims, 8 Drawing Sheets

DYNAMIC SOLVENT PERMITTIVITY INSTRUMENT

FIELD OF THE INVENTION

An instrument for measuring the dielectric constant of samples with complex or uncertain geometries that can include unusually shaped single sample pieces or collections of differently shaped sample pieces such as powders.

BACKGROUND OF THE INVENTION

The dielectric constant of irregularly shaped samples, or collections of small pieces of a sample type, often cannot be measured. This is because the conversion of a capacitance measurement to a dielectric constant requires exact knowledge of sample dimensions.

A number of cumbersome and notably inaccurate methods of estimating the dielectric constant of samples with complex geometry are currently used. But, their shortcomings are widely acknowledged and are often not utilized because of their questionable results. These methods require the application of assumptions concerning the additivity of dielectric constants of mixtures when the sample is mixed with materials such as epoxy resins in proportions which must be known with precision.

SUMMARY OF THE INVENTION

A broad aspect of the present invention is an apparatus for measuring a dielectric constant of a sample containing:

a first capacitor having a first space; a second capacitor having a second space to contain the sample; and a means for adding a material in the first space and to that portion of the second space not occupied by the sample until the dielectric constant of the first space is equal to the dielectric constant of the second space.

Another broad aspect of the present invention is an apparatus for measuring the dielectric constant of a sample containing a first capacitor having a first space between a pair of plates within which the sample is disposed; a second capacitor having a second space between a pair of plates; a container; the first capacitor and said second capacitor are disposed in the container;
a means for adding a solution having a first dielectric constant to the container so that the first space is filled with the medium and that part of the second space not occupied by the sample is filed as the solution; and a means for adding to said solution a second solution having a second dielectric constant to adjust the dielectric constant of said first space and said second space until said dielectric constant of said first space and said second space are equal.

DETAILED DESCRIPTION

The technique described here utilizes no assumptions but is a direct measurement technique, and requires no knowledge of sample size, weight, or volume. Thus, the technique described here provides values with greater accuracy and convenience than previous techniques.

Figure 1:
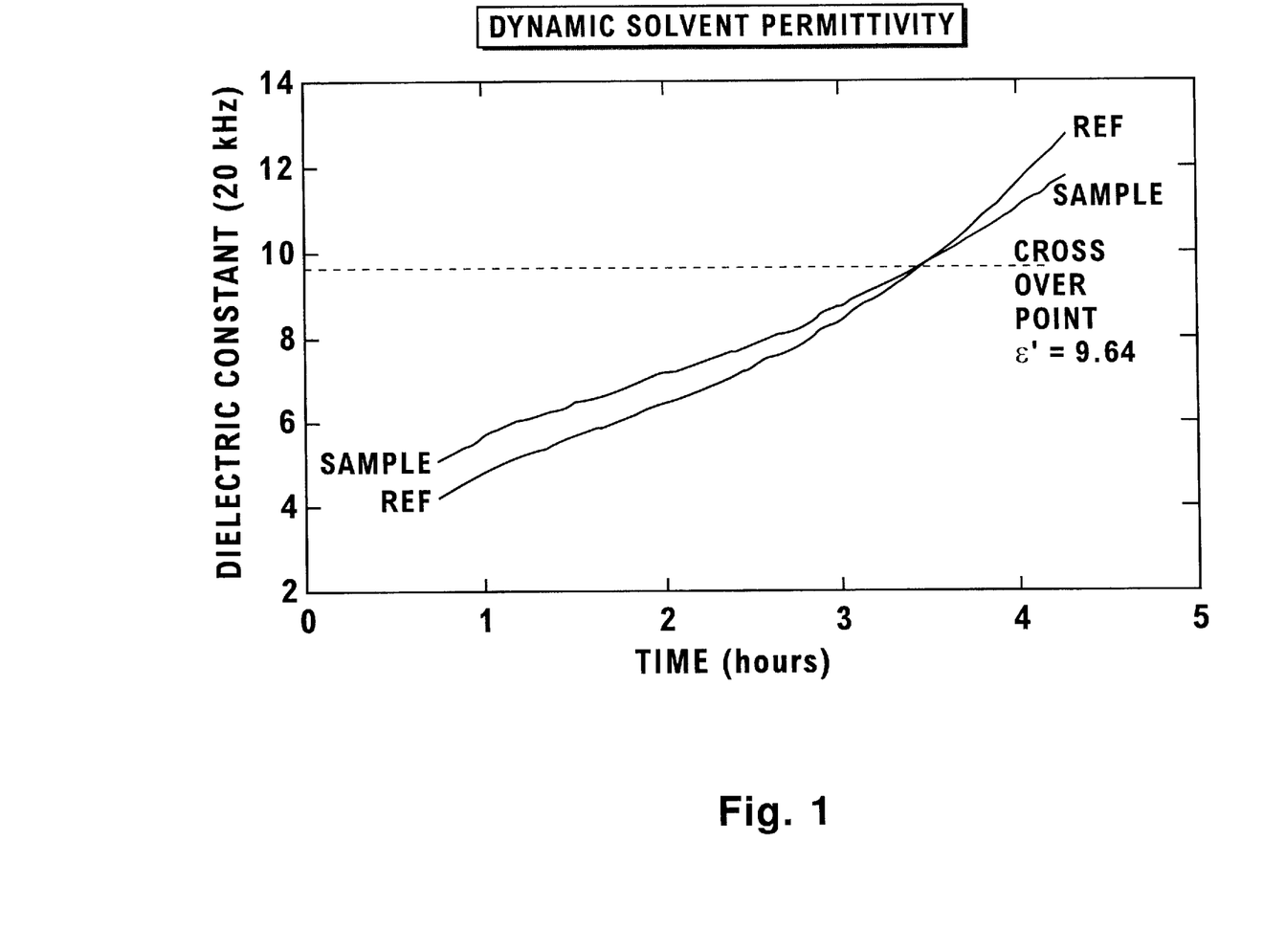
FIG. 1 Data from a DSP experiment showing the measured dielectric constant of the sample and reference cells as a function of time as the solvent medium changes. The crossover point of E'=9.64 provides the unknown's dielectric constant.

This invention allows measurement of complex samples by dynamically comparing the capacitance of two parallel plate fixtures. In the simplest case, the two fixtures share the same overall dimensions. One fixture contains the sample while the other remains empty. As the solvent mixture which surrounds both fixtures changes from one extreme of having a lower dielectric constant than the sample to one which a has higher dielectric constant, a point is reached where the capacitance of the sample and reference cells match, as shown in FIG. 1. The dielectric constant of this solvent mixture, which can be calculated because the dimensions of the empty reference cell are known exactly, is equal to the dielectric constant of the unknown sample.

Figure 2:
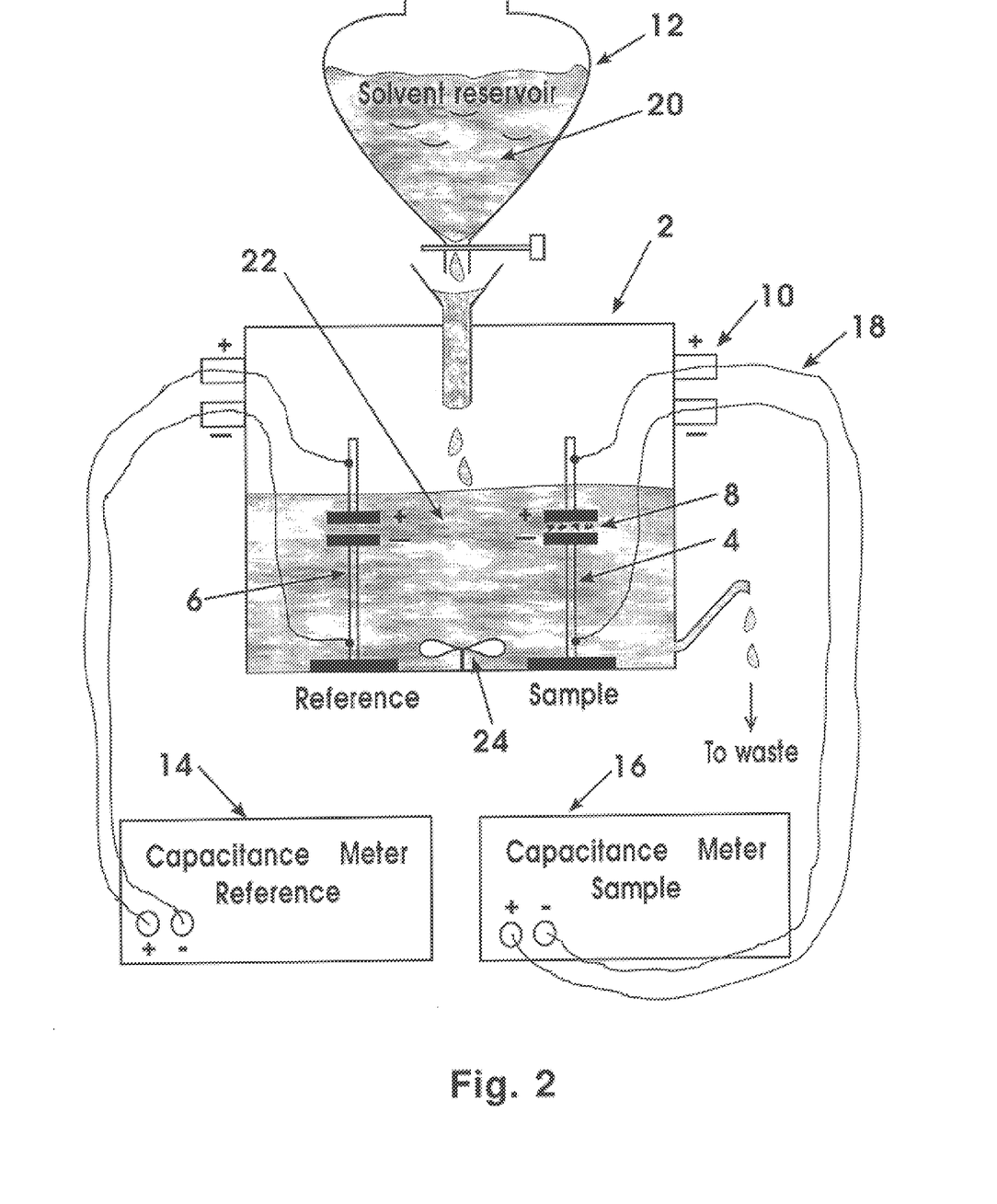
FIG. 2 Diagram of Dynamic Solvent Permittivity (DSP) Measurement instrument as originally conceived and implemented.

The sample arrangement consists of a fluid chamber common to both sample and reference capacitance fixtures, a solvent reservoir, a height-adjustable drain to adjust the fluid level, and electrical leads from each of the two sets of positive and negative terminals on the capacitance fixtures (FIG. 2).

This technique can be applied to samples where the sizes do not lend themselves to traditional techniques—such as granular powders and to samples that cannot be machined into known dimensions such as very brittle, hard, or precious materials.

Figure 3:
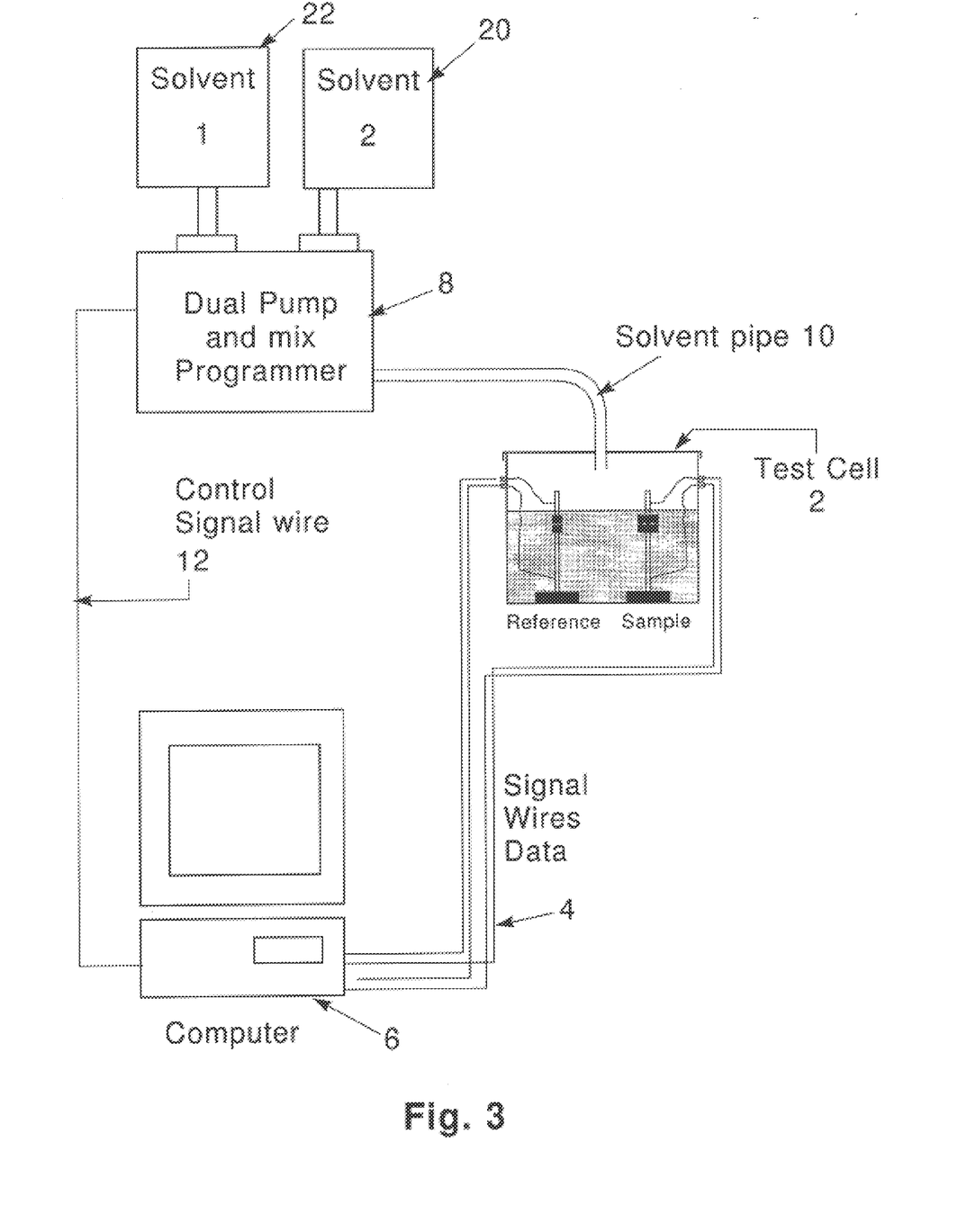
FIG. 3 Schematic diagram of DSP instrument using programmable solvent mixing pump and computer. Shows relationship of measurement cell to solvent reservoir, programmable mixing pumps and to computer which monitors mixing and compares input data signals from measurement cell until endpoint crossover is achieved.
Figure 4:
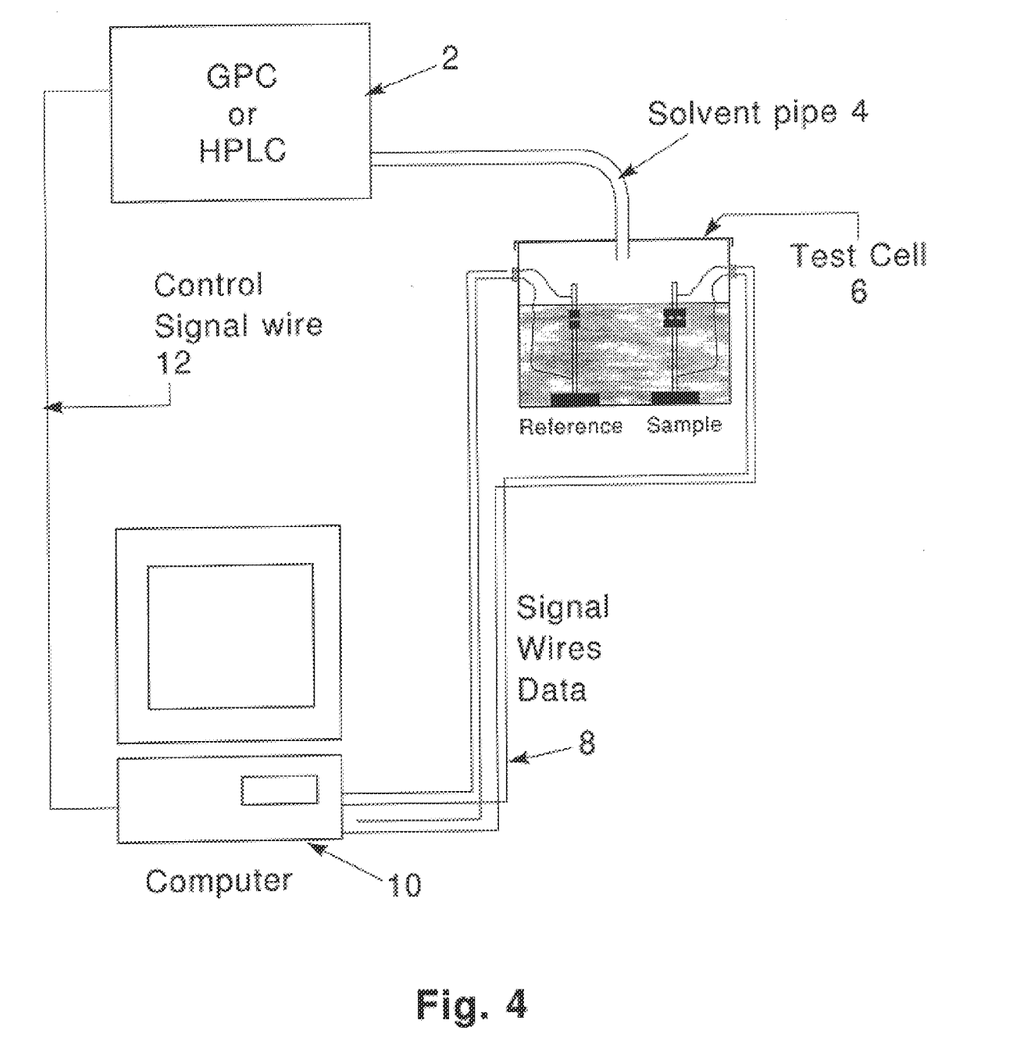
FIG. 4 Schematic diagram of DSP instrument using commercially available solvent mixing instrument like HPLC or GPC. Shows relationship of measurement cell to solvent reservoir and programmable mixing pumps and to computer which monitors mixing and compares input signals from measurement cell until endpoint crossover is achieved.

While this technique was implemented using a slow drip addition method, as shown in FIG. 2, the solvent comparison concept can easily be extended to continuous flow techniques. These would lend themselves to a new analytical technique utilizing the dual programmable pumps as used High Performance Liquid Chromatography (HPLC) or Gel Permeation Chromatography (GPC). Such arrangements are shown in FIGS. 3 and 4.

DESCRIPTION OF THE INVENTION: PREFERRED EMBODIMENTS

An example experiment starts with loading the sample fixture with an unknown amount of sample. The fluid chamber is then filled to a level submersing the fixtures with a solvent known to have a dielectric constant which is below that of the sample. As long as the dielectric constant of this liquid is known to be lower than the sample, there is no need to know its exact dielectric constant value. The solvent reservoir is then loaded with a second solvent which has a dielectric constant known to be higher than that of the sample. This second solvent should preferably be miscible with the first solvent to ensure good mixing. Non miscible solvents may also be used in conjunction with surfactants to compatibalize otherwise phase separated solvent mixtures.

The capacitance is measured and recorded for each of the fixtures separately. Then, the solvent reservoir is opened and a slow drip started. A stirring mechanism is preferably engaged to ensure good uniformity of mixing of the solvents. The capacitance of the reference and sample fixtures are measured at time intervals. The dielectric constant of the solvent mixture gradually changes as more of solvent 2 from the reservoir is mixed with solvent 1. A point is reached where the dielectric constant of the solvent mixture is equal to that of the sample. At this point the capacitance of the sample and reference fixtures will be equal, as shown schematically in FIG. 5. Then, using this capacitance value, the dielectric constant for the geometry of the reference cell is calculated. This is also then the dielectric constant of the unknown sample.

In addition to the cell designs discussed thus far, many other designs based on the same principle can be envisaged by those skilled in the art. These include flow through cells where the sample and reference capacitor plates (or equivalent active components) are of different size and/or shape. This will allow greater flexibility in designing the cell. In order to facilitate comparison between the sample and reference cells, appropriate geometric factors would have to be incorporated into the comparison circuit or algorithm used to determine the point at which the sample and reference cell contents have dielectric constants which are equal. For example, if the sample capacitor plate were 2 cm in diameter, and the reference plate were 1 cm in diameter, and they had equal gaps, then the dielectric constants of the sample and reference would be equal when the capacitances (C) held the relationship that C(samp)=4×C(ref). This follows from the relationship of capacitance to dielectric constant. E'=(Capacitance×gap width)/(Area of plate)

Figure 6:
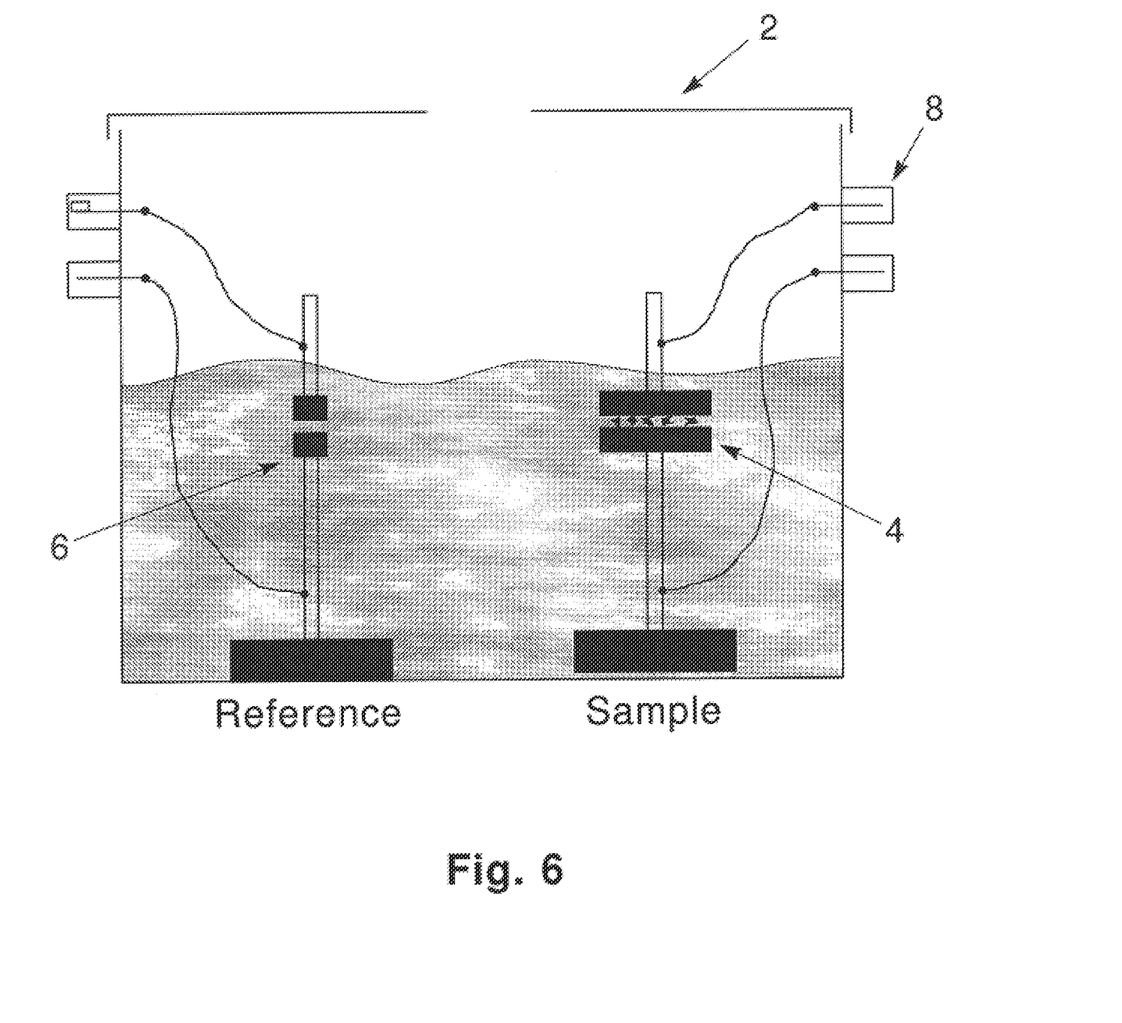
FIG. 6 Illustrates that the sample and reference capacitance plates need not be of identical geometry.

Further, there is no requirement that the sample and reference capacitance plates have any particular placement relationship to one another within the cell as long as the solvent mixture uniformity was great enough to allow the assumption that the solvent mixture was essentially the same at each at a particular point in time. An example is shown in FIG. 6. In addition, FIG. 7 of a flow through cell type shows a second reference electrode by which the assumption of solvent uniformity within the cell could be tested. Further, the use of the second reference capacitor in this flow-through cell design would allow averaging the capacitances of the two references. This averaged result could then be used to compare to the sample thus eliminating any error associated with solvent gradient in the direction of flow.

Further, this technique lends itself to being carried out with the use of other commonly available instruments which can provide programmable control over solvent mixing such as an HPLC (High Performance Liquid Chromatograph) or GPC (Gel Permeation Chromatograph). If these instruments were available, only the measurement cell and the comparison algorithm would need to be provided to allow the dynamic solvent permittivity measurement to be completed. Thus, the most difficult experimental portion of a DSP measurement, the solvent mixing, could be handled by commercially available instrumentation.

This technique could be extended to permittivity measurements in the microwave frequency range using waveguides and resonance perturbation techniques and sequentially measuring sample and reference for each of a range of solvent mixtures. Again the match point would provide the unknown dielectric constant.

This could be accomplished using two side by side waveguide resonance chambers separated by a screen which isolates each chamber to microwave radiation but allows solvent to flow freely ensuring uniform solvent composition. The dielectric constant of each chamber can be periodically measured and compared. When equal for both chambers then the dielectric constant of the sample is then known.

Figure 8:
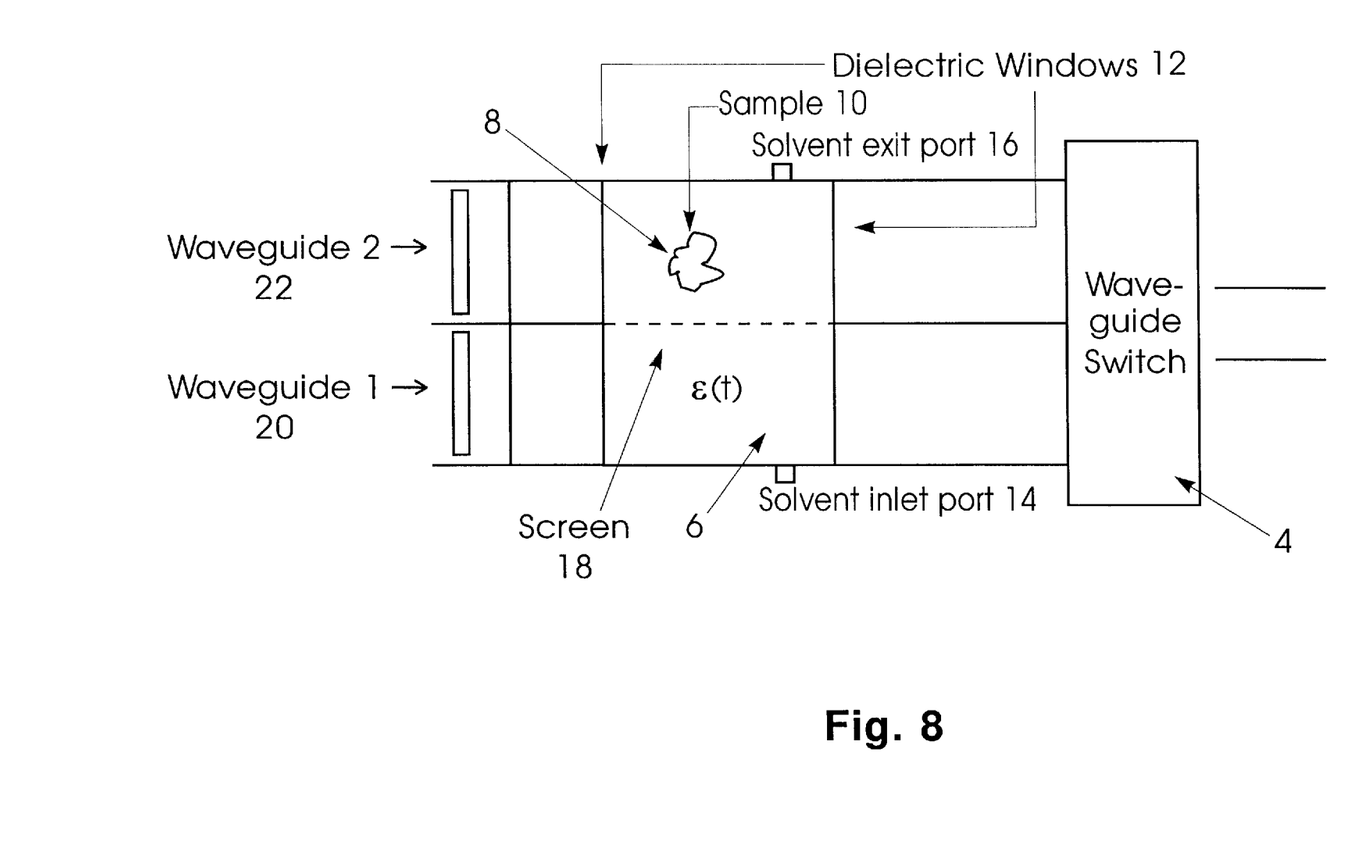
FIG. 8 Shows sample and reference cells in microwave frequency waveguide cells. Solvent can enter and exit the two compartments and move between them freely via a solvent permeable, but microwave barrier screen. Illustrates that the DSP technique can be utilized with techniques other than capacitance for measurement of dielectric constant.

The microwave apparatus in FIG. 8 is operated in a manner similar to the parallel plate apparatus described earlier. A microwave switch is used to switch between 2 different waveguide sample chambers. The input impedance of each chamber is measured and compared to that of the other chamber. A screen or fine mesh is used to allow the dielectric fluid into both chambers, thus when the dielectric constant of the surrounding fluid is equal to that of the test sample, the input impedance of both waveguides will be identical and the dielectric constant of the sample can be determined.

This technique can be used with any type of waveguide structure. This includes but is not limited to rectangular waveguide, circular waveguide, elliptical waveguide, coaxial waveguide, and ridged waveguide. In addition, any structure that allows the controlled and repeatable measurement of microwave impedance can be used with this technique.

This kind of structure and technique allows measurements at high microwave and millimeter wave frequencies. Normally these measurements are extremely difficult because the sample is required to completely fill the waveguide structure or you must account for interaction between the microwave or millimeter wave and the physical shape and size of the structure. Using this technique, measurements from 300 Mhz to 1 Thz (1000 Ghz) should be possible.

The total frequency range measurable using the Dynamic Solvent Permittivity technique by either the capacitance or microwave impedance method is 10 Hz to 1000 GHz.

One particular experiment used Alumina ($Al_2O_3$) shards as the sample, ethyl ether as solvent 1 and ethyl alcohol as solvent 2. Capacitance measurements of both reference and sample cells were made at 5 minute intervals. The progression of the dielectric constants of the reference and sample cell contents can be seen in FIG. 1. The crossover point occurs at a dielectric constant of 9.644, which is thus the measured dielectric constant of the unknown. This value is in excellent agreement with literature values of the dielectric constant of Alumina ($Al_2O_3$).

Description of FIG. 1—Dynamic Solvent Permittivity experimental data

FIG. 1 shows a plot of the dielectric constant vs. time of both the sample and reference of an experiment run using the prototype instrument shown schematically in FIG. 2. This trial used crushed Al2O3 pieces as the sample, ethyl ether as the initial solvent and ethyl alcohol as the second solvent. As the second solvent was slowly added to the experimental chamber containing the sample and reference electrode assemblies, the capacitance and the corresponding dielectric constant was followed and plotted. A crossover point is reached where the capacitance of the sample and reference are equal, which determines the dielectric constant of the unknown.

Description of FIG. 2—Dynamic Solvent Permittivity prototype

FIG. 2 shows the Dynamic Solvent Permittivity setup used in the laboratory trials. It also constitutes a prototype DSP system. A main solvent chamber (2) contains both a sample electrode (4) assembly and a reference electrode (6) assembly, each of which consists of two parallel conducting metallic plates. Within the sample electrode is inserted a sample material (8), which is the material piece or pieces for which a dielectric constant value is desired. Additionally, a stirring mechanism (24) may be in place. Initially, the sample chamber is filled with a solvent (22) which has a dielectric constant known to be lower than the sample. A second solvent (20) which is known to have a dielectric constant higher than the sample. (Alternatively, 22 could be higher and 20 could be lower). A mechanism for slowly introducing the second solvent 20 into the sample chamber 2 to mix with the first solvent 22 is an addition funnel (12). The sample electrode assembly 4 is connected to a capacitance meter (16) and likewise the reference electrode is connected to a capacitance meter (14).

Description of FIG. 3—Schematic of DSP using programmed solvent sources and computer data collection and analysis FIG. 3 shows a dynamic solvent permittivity set up utilizing programmable solvent pump 8, first solvent 22, second solvent 20, test chamber 2 which contains both sample and reference electrode assemblies, signal wires 4, computer for analysis and program control 6, and control signal wires 12. Additionally, a single tube or pipe containing the solvent mixture 10 delivers solvent from the programmable pump 8 to the test chamber 2.

Description of FIG. 4—Schematic of DSP using gel permeation chromatograph (GPC) or high performance liquid chromatography HPLC instrument as solvent mixer and pump In this configuration, the programmable solvent mixing is carried out by commercially available solvent mixing systems (GPC or HPLC) 2, solvent mixture is delivered to the sample test chamber 6 by tube 4, and sample and reference capacitance signals conducted to the computer by wire set 8, to computer 10 for analysis and control of solvent pumps via control signal wires 12.

This diagram essentially shows how the DSP instrument could be incorporated into GPC or HPLC instruments as an analytical add-on tool.

Figure 5:
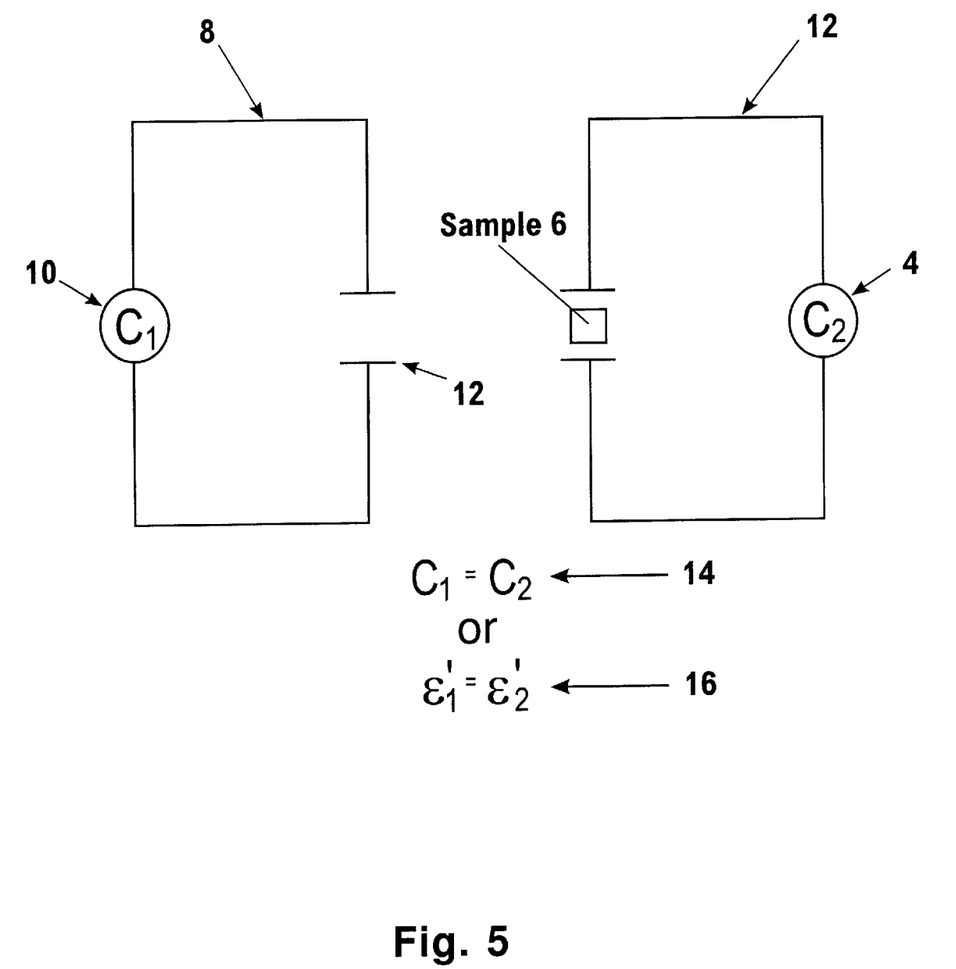
FIG. 5 Schematic diagram of two capacitance circuits, the reference C1 and Sample C2, which are submerged in common solvent medium. The endpoint occurs when the capacitance of the two circuits become equal (assuming plate geometries are the same). This then allows calculation of dielectric constant from $E'=(C)(d)/A$, where C=capacitance, d=the gap between plates, and A=area of capacitor plates.

Description of FIG. 5—Schematic of end-point condition

A schematic diagram of the sample capacitance circuit 2 includes the sample electrode assembly 2 where the sample is placed and the capacitance bridge 4 where the capacitance is measured. The diagram also shows the corresponding reference circuit 8 which included the empty electrode assembly 12 and the capacitance bridge 10 where the capacitance is measured. Also shown are the endpoint conditions where the capacitance of the sample electrode equals the capacitance of the reference electrode—for the case where the sample and reference electrode assembly geometries are the same 14. More generally, if the geometries of the sample and reference electrode assemblies differ, the endpoint can be specified as the point at which the total combined dielectric constant of the solvent plus sample within the sample electrodes is equal to the dielectric constant of the solvent within the reference electrode 16.

Description of FIG. 6—Illustrating that the sample and reference capacitance plates need not be of identical geometry.

The solvent container 2 includes the sample electrode assembly 4 and the reference electrode assembly 6 which is not necessarily of the same size or shape as that of the sample electrode assembly. Figure also points out electrical connectors 8 by which the electrodes of the sample and reference assemblies send electrical signals to the capacitance meter or other device intended to compare the endpoints.

Figure 7:
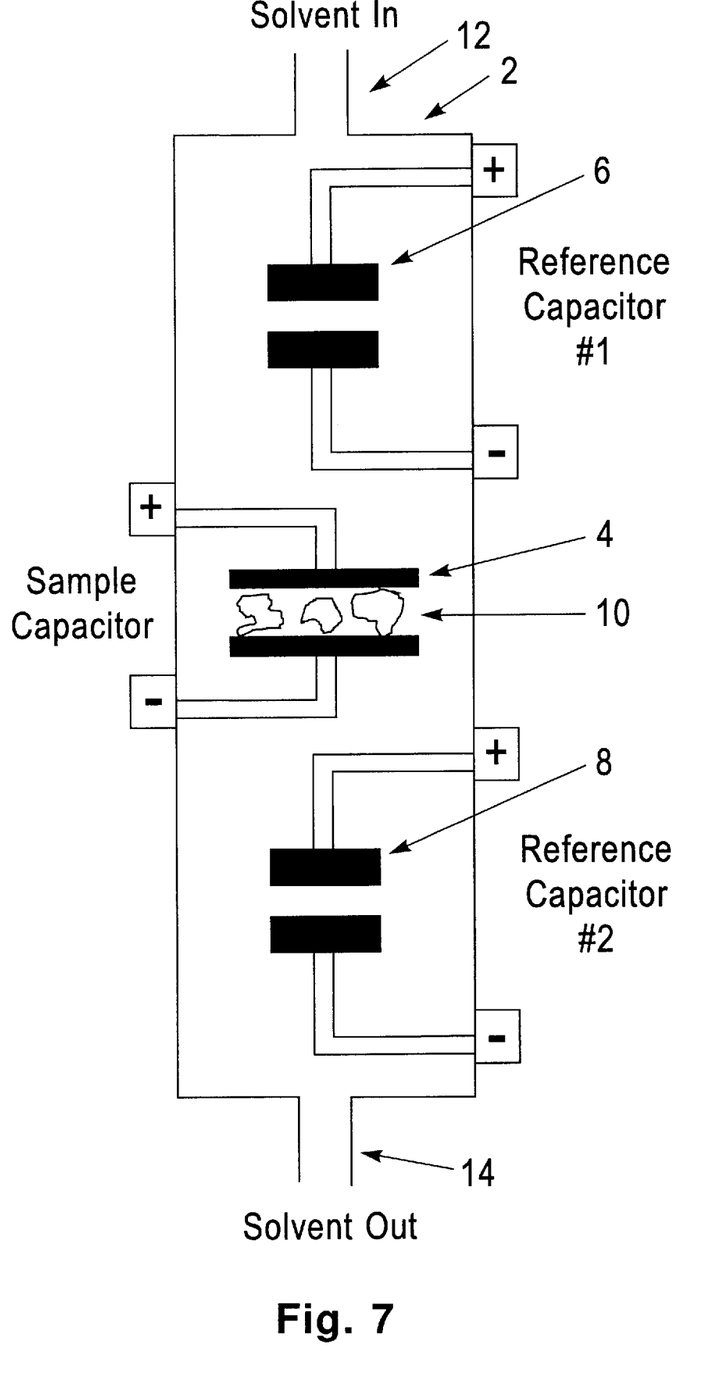
FIG. 7 Illustrates that sample and reference capacitance plates can be physically oriented wrt each other in ways other than side-by-side, and that a second reference can be utilized for maximum accuracy.

Description of FIG. 7—Illustrating that sample and reference capacitance plates can be physically oriented wrt each other in ways other than side-by-side, and that a second reference can be utilized for maximum accuracy.

There are circumstances where the sample and reference electrode assemblies would be more conveniently or more advantageously oriented differently than the side by side configuration previously shown. And in addition, there are circumstances where two reference electrode assemblies straddling the sample electrode assembly may prove advantageous to the accuracy of the measurement. When there is a solvent gradient from the solvent entry side of the cell to the solvent exit side, two references can be used to eliminate inaccuracies caused by uncertainties in the solvent gradient field. This figure shows a housing 2 which contains solvent and solvent mixtures, a reference electrode assembly 6, a sample electrode assembly 4, irregularly shaped sample particles 10, and a second reference electrode assembly 8. In addition it shows a port for solvent ingress 12, and a port for solvent egress 14.

Description of FIG. 8—Shows sample cell 8 and reference cell 6 in microwave frequency waveguide assemblies 20 and 22. The sample 10 sits inside the sample waveguide cavity 22. Solvent and solvent mixtures are introduced through port 14 and exits through port 16. The screen 18 creates an electrical separation between the sample waveguide assembly 22 and the reference waveguide assembly while allowing unimpeded flow of solvent from one cell to the other. The waveguide switch allows sequential probing of the dielectric properties of the sample 22 and reference 20 cells which is necessary for comparing the dielectric properties of the two cells in anticipation of the endpoint which occurs when the dielectric constant of the two cells is equal. More precisely, the endpoint in the case of a resonance perturbation type microwave frequency dielectric measurement is when the resonance frequency shift for the sample chamber is equal to the resonance frequency shift of the reference chamber—in the case of equal cell dimensions.

While the present invention has been shown and described with respect to a preferred embodiment, it will be understood that numerous changes, modifications, and improvements will occur to those skilled in the art without departing from the spirit and scope of the invention.

We claim:

1. An apparatus for measuring the dielectric constant of a sample having a fixed geometrical shape comprising:

a container for holding a common medium, a sample, a first capacitor and a second capacitor;

said first capacitor having a first space between plates of said first capacitor;

said second capacitor having a second space between plates of said second capacitor and made to accommodate a sample within said second space, means for adding a medium to said first space and the portion of the second space unoccupied by the sample;

a means to modify the constitution of said medium added to said container to modify the dielectric constant of said medium until the capacitance of said first capacitor becomes equal to the capacitance of said second capacitor;

means for measuring said capacitance of said first capacitor and said capacitance of said second capacitor as said constitution of said medium is modified until said first capacitance is equal to said second capacitance so that the dielectric constant of said medium as determined from the value of said first capacitance and second capacitance when said first and said second capacitance are equal is the dielectric constant of said sample.

2. An apparatus according to claim 1 wherein said apparatus is contained in a miniature cell type to accommodate small amounts of sample.

3. An apparatus according to claim 1 wherein said apparatus further includes means for continuously changing the composition of said medium.

4. An apparatus according to claim 1 wherein said medium is a gas.

5. An apparatus according to claim 1 wherein said apparatus further includes a means for determining the capacitance of said first capacitor and the capacitance of said second capacitor and further including a means to determine a first dielectric constant for the material between the plates of said first capacitor and a second dielectric constant for the material between the plates of said second capacitor and a means to determine when said first dielectric constant is the same as said second dielectric constant which value is the dielectric constant of said sample.

6. An apparatus according to claim 5 wherein said apparatus further includes means for measuring at a microwave frequency said first and said second capacitances by a side by side waveguide measurement of said first and said second capacitors.

7. An apparatus according to claim 1 wherein said said first capacitance and said second capacitance are measured by a method using two separate instrument sets.

8. An apparatus according to claim 1 wherein said medium is a flowable medium and said aparatus has on input port and an exit port to flow said medium into and outfrom said chamber.

9. An apparatus for measuring the dielectric constant of a sample having a fixed geometrical shape comprising:

a first capacitor having a first space between a pair of plates within which said sample is disposed;

a second capacitor having a second space between a pair of plates;

a container;

said first capacitor and said second capacitor are disposed in said container;

means for adding a medium having a first dielectric constant to said container so that said first space is filed with said medium and that part of said second space not occupied by said sample is filed as the said solution;

means for adding to said medium a second medium having a second dielectric constant to adjust the dielectric constant of said first space and said second space until said dielectric constant of said first space and said second space are equal so that the capacitance of said first capacitor is equal to the capacitance of said second capacitor.

10. An apparatus for measuring a dielectric constant of a sample having a fixed geometrical shape comprising:

a first capacitor having a first space;

a second capacitor having a second space to contain said sample;

means for adding a material in said first space and to that portion of said second space not occupied by said sample until the dielectric constant of said first space is equal to the dielectric constant of said second space so that the capacitance of said first capacitor is equal to the capacitance of said second capacitor.

11. An apparatus according to claim 5 wherein said means to determine is a computer.

12. An apparatus according to claim 1 wherein said first capacitor is a reference capacitor, said apparatus comprises a plurality of reference capacitors.

13. An apparartus according to claim 1 wherein said container has a first compartment containing said first capacitor and a second compartment containing said second capacitor.

14. An apparatus according to claim 13 wherein said first compartment and said second compartment are separated by partition perrmiting said fluid to flow between said first and said second compartments.

15. An apparatus according to claim 13 wherein said first compartment is a first wave guide and said second compartment is a second waveguide and means to flow said medium within said first and said second waveguides.

16. An apparatus for measuring the dielectric constant of a sample comprising:

a first waveguide having a first space within which said sample is disposed;

a second wave guide having a second space;

means for adding a flowable medium having a first dielectric constant to said first space so that said first space is filled with said medium and to said second space so that, the part of said second space not occupied by said sample is filed as the said flowable medium, means for adding to said flowable medium a second flowable medium having a second dielectric constant to adjust the dielectric constant of said first space and said second space until said dielectric constant of said first space and said second space are equal.

17. An apparatus according to claim 1 wherein said fixed geometrical shape is a single object.

18. An apparatus according to claim 9 wherein said fixed geometrical shape is a single object.

19. An apparatus according to claim 10 wherein said fixed geometrical shape is a single object.

20. An apparatus according to claim 16 wherein said fixed geometrical shape is a single object.

21. An apparatus according to claims 1, 9, 10 or 16 wherein said fixed geometrical shape is a plurality of objects.

22. An apparatus according to claim 1 wherein said first and said second capacitances are measured utilizing a switch to alternately measure one of said first and said second capacitances followed by the other using the same instrument.

* * * * *